United States Patent [19]

Borror et al.

[11] 3,976,640

[45] Aug. 24, 1976

[54] BIS-TYPE QUATERNARY SALTS INCLUDING BENZOTHIAZOLE AND BENZIMIDAZOLE RINGS AND PROCESS FOR PREPARING DYE THEREWITH

[75] Inventors: Alan L. Borror, Lexington; Louis Cincotta, Andover, both of Mass.

[73] Assignee: Polaroid Corporation, Cambridge, Mass.

[22] Filed: Feb. 18, 1975

[21] Appl. No.: 550,182

[52] U.S. Cl. .......................... 260/240.1; 260/304 R
[51] Int. Cl.² ............... C07D 417/12; C07D 417/06
[58] Field of Search ..................... 260/304 C, 240.1

[56] References Cited

UNITED STATES PATENTS

| | | | |
|---|---|---|---|
| 3,573,289 | 3/1971 | Straley et al. | 260/240.1 X |
| 3,674,782 | 7/1972 | Eldredge et al. | 260/240.1 X |
| 3,836,370 | 9/1974 | Beretta et al. | 260/240.1 X |

*Primary Examiner*—Allen B. Curtis
*Attorney, Agent, or Firm*—Mart C. Matthews; Philip G. Kiely

[57] ABSTRACT

Novel bis type heterocyclic quaternary salts are provided which are useful in the preparation of various linked cyanine dyes and related compounds.

10 Claims, No Drawings

BIS-TYPE QUATERNARY SALTS INCLUDING BENZOTHIAZOLE AND BENZIMIDAZOLE RINGS AND PROCESS FOR PREPARING DYE THEREWITH

BACKGROUND OF THE INVENTION

1. Field of the Invention

This invention relates to chemistry and, more particularly, to novel double or "bis-type" quaternary salts of heterocyclic bases and processes useful in the synthesis of various linked cyanine dyes and related compounds.

2. Description of the Prior Art

Most of the reactions leading to cyanine dyes and those compounds related to them are of the condensation type wherein two active dye intermediates react under suitable conditions with the elimination of some simple molecule, such as mineral acid, mercaptan, alcohol, water, aniline or acetanilide. These intermediates fall into two categories: (1) those containing reactive hydrogen, and (2) those containing a reactive group, such as halogen, cyano, alkyl- or arylmercapto, alkoxy, anilino, or acetanilido, which is capable of dye condensation with the reactive hydrogen of the first component.

In the synthesis of "true" cyanine materials, intermediates of the first type are usually quaternary salts of heterocyclic bases containing a reactive methyl group, which react through the formation of a methylene base resulting from the loss of a proton. Components of the second type are also frequently quaternary salts of heterocyclic bases, but having a proton seeking (negative) atom or group linked to the α- or γ-atom of the heterocyclic nucleus either directly or through a vinylene or polyvinylene chain. In another type of reaction, two equivalents of the above-mentioned heterocyclic quaternary salt having a reactive methyl group may be condensed together through a component which provides the central part of the conjugated chain, e.g., ethyl orthoformate, giving rise to a symmetrical cyanine dye molecule.

In compounds related to the cyanines, e.g., those dyestuffs containing an amidinium ion or amidic chromophoric system, only one of the above-mentioned types of intermediate may comprise a heterocyclic quaternary salt. For example, hemicyanine materials may be prepared by treating a heterocyclic quaternary salt having one of the aforementioned reactive negative substituents with an aromatic or an aliphatic amine containing the replaceable hydrogen, or p-dialkylaminostyryl dyes may be prepared by condensation of the appropriate heterocyclic quaternary salt containing a reactive methyl group with p-dialkylamino-benzaldehyde.

Intermediates in the synthesis of cyanine dyes comprising at least two quaternary heterocyclic cyanine dye nuclei linked by a divalent hydrocarbon radical have previously been described in the art, for example, see U.S. Pat. Nos. 2,393,351; 2,425,772; 2,425,773; 2,461,139; 2,465,744; 2,592,196; and 3,622,317. These intermediates are disclosed as being useful in the synthesis of bis, polymeric or pseudopolymeric cyanine dyes, and are generally characterized as having a hydrocarbon linking moiety, e.g., an alkylene group, connecting the quaternized nitrogens of similar heterocyclic nuclei. These bis-type quaternary salts of the prior art are to be distinguished from those of the present invention in that the present compounds comprise an amide bond linking moiety between the cyanine dye segments, and said moiety is not attached to the quaternized nitrogens. In general, the compounds of this invention are more readily synthesized in better yields by virtue of the aforementioned amide linking moiety than bis-type quaternary salts of the prior art.

SUMMARY OF THE INVENTION

In accordance with the present invention, novel bis-type quaternary salts are provided which may be employed in the synthesis of a wide variety of linked cyanine dyes and related compounds. In general, the novel compounds of the invention comprise two linked heterocyclic quaternary salt segments, each containing a reactive methyl group in alpha or gamma position to the quaternary nitrogen atoms of the respective nuclei. The segments are linked together through a novel amide containing bridging group attached at each end to a nuclear atom other than the quaternized nitrogen of the salt segment.

The alkylene-amide bridging or linking group is particularly advantageous over linking groups employed in previous bis-type quaternary salts in that the individual heterocyclic segments are readily joined through the formation of an amide bond, the length of the chain is easily changed to suit particular needs and the group is stable throughout the various dye condensation reactions employed to form cyanine dyes and related compounds. Since each heterocyclic salt segment includes a reactive methyl substituent, the novel bis-type compounds of the invention may be condensed with the appropriate conventional dyestuff intermediates to provide a wide variety of linked cyanine dyes and related materials.

The novel compounds of the invention may be represented by one of the formulae:

I.
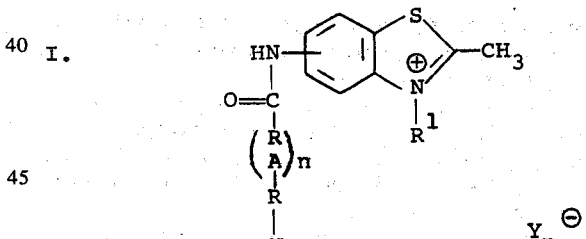
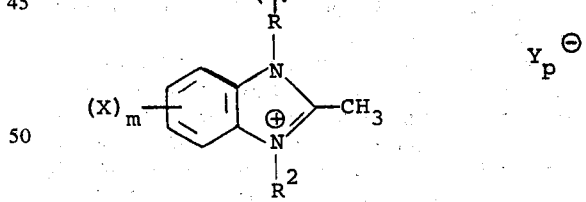

II.
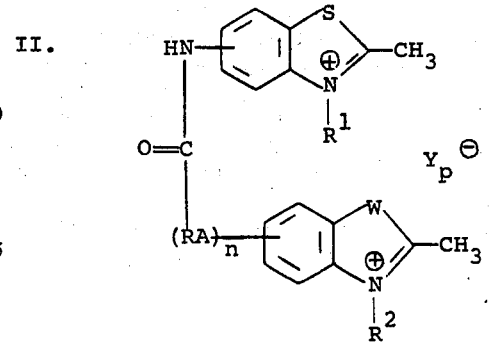

wherein R is an alkylene group having from 1 to 5 carbon atoms, e.g., $-(CH_2)_2-$, $-(CH_2)_3-$, etc.; A is a divalent amide group, i.e.,

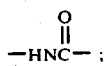

$R^1$ and $R^2$ are each a lower alkyl group, i.e., a 1 to 4 carbon alkyl group such as methyl, ethyl, etc., a sulfoalkyl group, e.g., sulfpropyl, sulfobutyl, etc., or a carboxyalkyl group, e.g., carboxymethyl, carboxyethyl, etc.; W is S or N—T wherein T is a lower alkyl group; X is a hydrogen atom, halogen atom, e.g., chloro, bromo, fluoro, etc., cyano group or a carbalkoxy group, e.g., carbmethoxy, carbpropoxy, etc.; Y is an acid anionic radical, e.g., haide, p-toluenesulfonate, etc.; $n$ and $p$ are each 0, 1 or 2; and $m$ is 1 or 2.

DETAILED DESCRIPTION OF THE INVENTION

It should be understood that all formulae set forth herein, such as Formulae I and II above, represent only an illustration of one form of structure, and that the actual structure of the depicted compound may in fact be a resonance hybrid of a series of structures in accordance with known principles in the art. Hence, a bis-type quaternary salt of Formula I or Formula II might actually have one or two ternary nitrogen atoms, depending upon the distribution of double and single bonds in the structure, and other structures shown herein as being charged may in fact show a resonance between a charged and uncharged structure. Since the term "bis" denotes a completely symmetrical molecule, the compounds of the present invention are characterized as "bis-type" because each quaternary salt segment need not be the same, as shown in Formulae I and II.

As examples of suitable substituents $P^1$ and $R^2$, mention may be made of lower alkyl groups (1 to 4 carbon alkyl groups) such as methyl, ethyl, propyl, isopropyl, butyl, and isobutyl; carboxyalkyl groups such as carboxymethyl, α-carboxyethyl, β-carboxyethyl, γ-carboxypropyl, δ-carboxybutyl, etc.; and sulfoalkyl groups such as sulfomethyl, β-sulfoethyl, γ-sulfopropyl, δ-sulfobutyl, p-sulfobenzyl, etc.

Y represents the anionic acid radical or radicals customarily employed in the cyanine dye art to balance the positive change of the quaternary nitrogen such as, for example, halide, i.e., chloride, bromide, iodide; methylsulfate; p-toluenesulfonate; benzenesulfonate; acetate; propionate; cyanate; perchlorate; etc. When subscript $p$ is 2, Y represents the two anionic radicals necessary to satisfy the positive charges on the quaternary nitrogen atoms of each heterocyclic salt segment. The individual heterocyclic segments may also exhibit an "internal salt" or "zwitterion" form wherein the anion takes the form of a negatively charged group in substituent $R^1$ or $R^2$, e.g., $-SO_3^\ominus$ or $-COO^\ominus$. In the latter case, there may be no external anion ($p=0$) or one external anion ($p=1$) depending upon whether one or both heterocyclic segments exhibit the internal salt form.

The length of the linking chain between heterocyclic salt segments may be varied depending on the value of $n$, that is, the number of amide and alkylene groups in the chain, and on the number of carbon atoms in the alkylene groups. Longer linking chains may tend to decrease the solubility of the compound and also may decrease the efficiency of photon excited energy transfer through the molecule, whereas shorter chains may tend to increase any steric hinderance problems during synthesis of the various dye derivatives. Preferably, $n$ is limited to 1 or 2, with the size of the alkylene group R ranging from 1 to 5 carbon atoms.

As specific examples of some preferred bis-type quaternary salts within the scope of this invention, mention may be made of the following compounds, which are listed for the purposes of illustration and are not intended to limit the invention:

A.

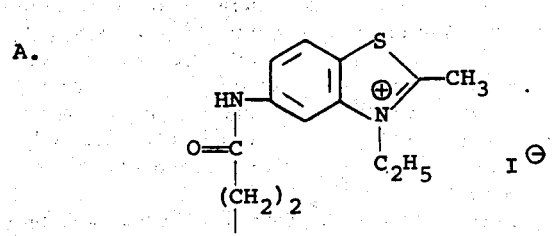

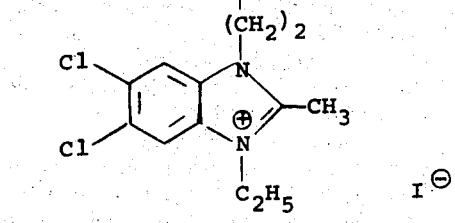

B.

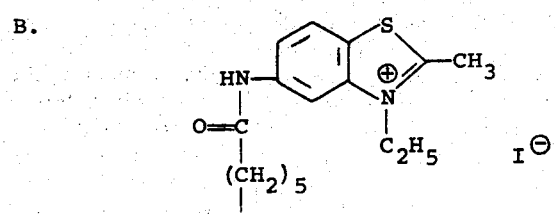

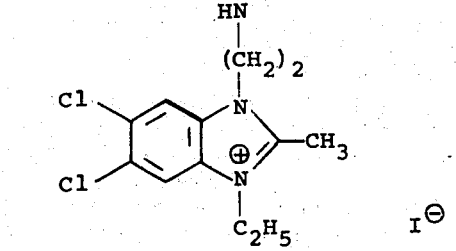

C. 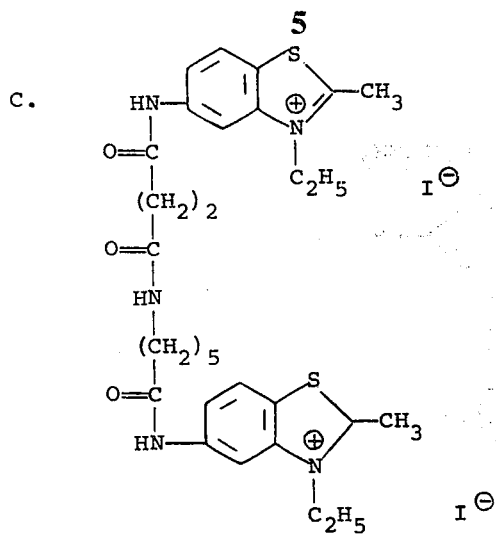

The novel compounds of the invention are readily prepared by reacting in a known and conventional manner, a primary amino-substituted quaternary salt of the formula:

III. 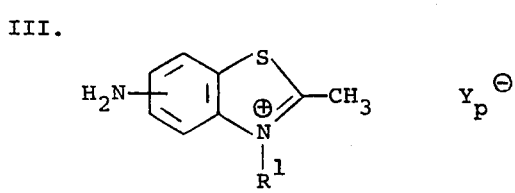

with a carboxylic acid-substituted quaternary salt of the formula:

IV.

or

V.

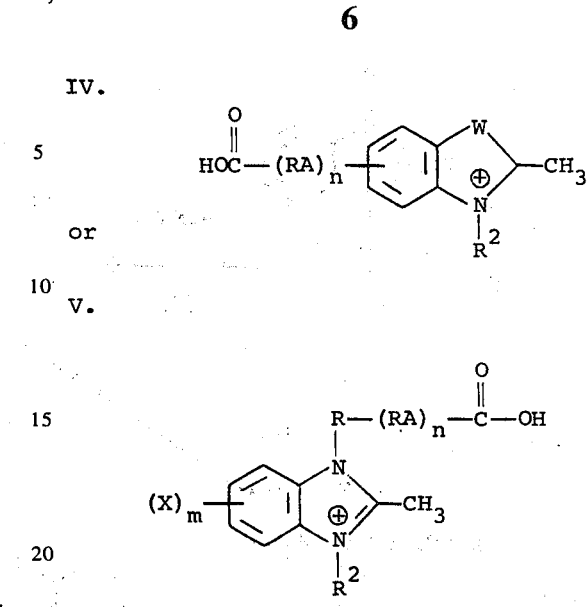

wherein all moieties are as defined for Formulae I and II.

The length of the linking group may be built up by conventional chemical reactions prior to the above linking reaction. To illustrate, a representative synthesis of a preferred compound is set forth below without intending to limit the invention to the details set forth therein.

EXAMPLE I

Formation of a bis-type quaternary salt intermediate ("double quat"):

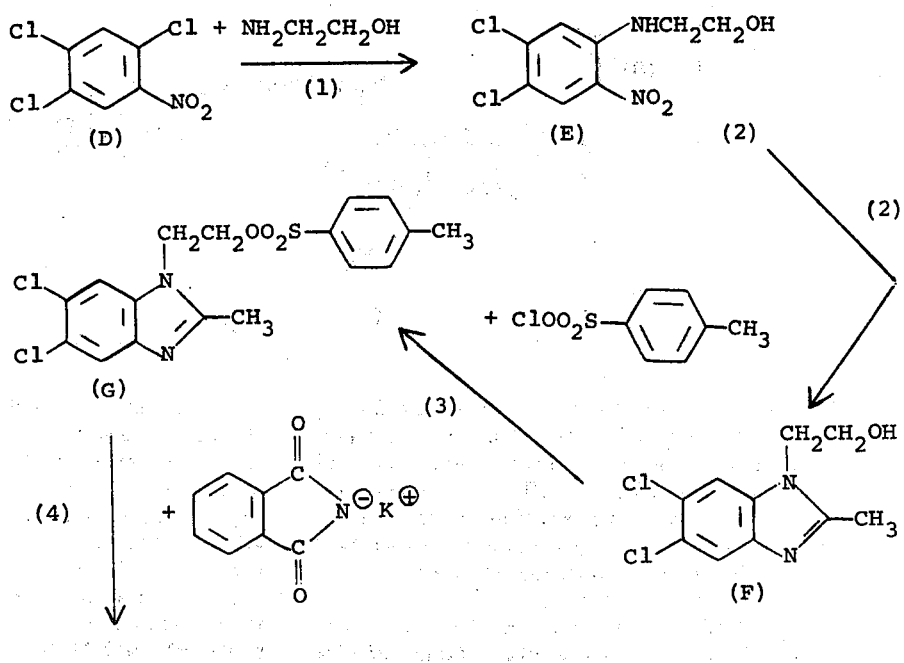

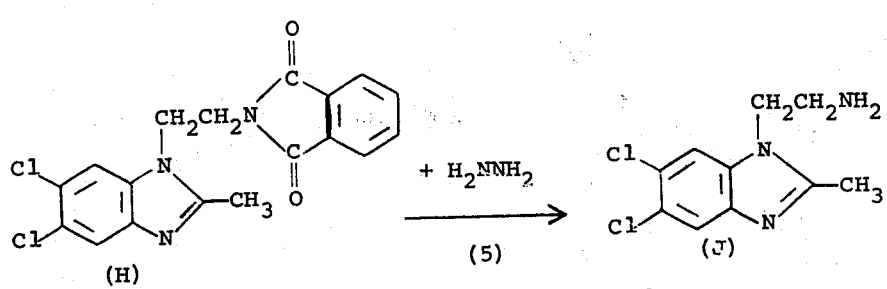

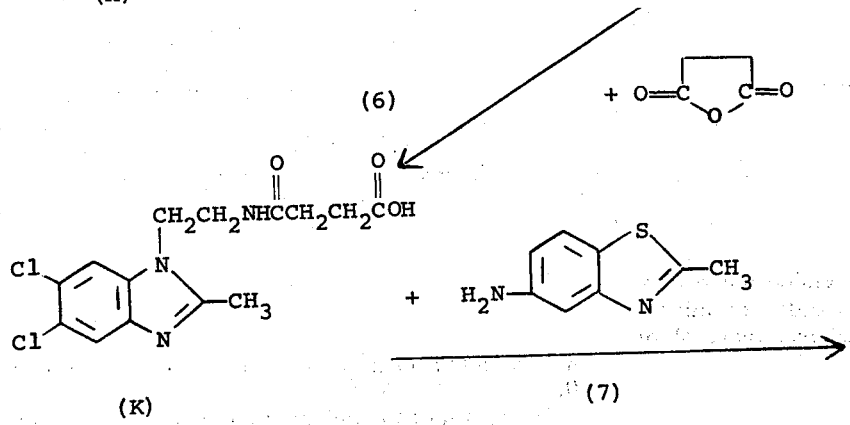

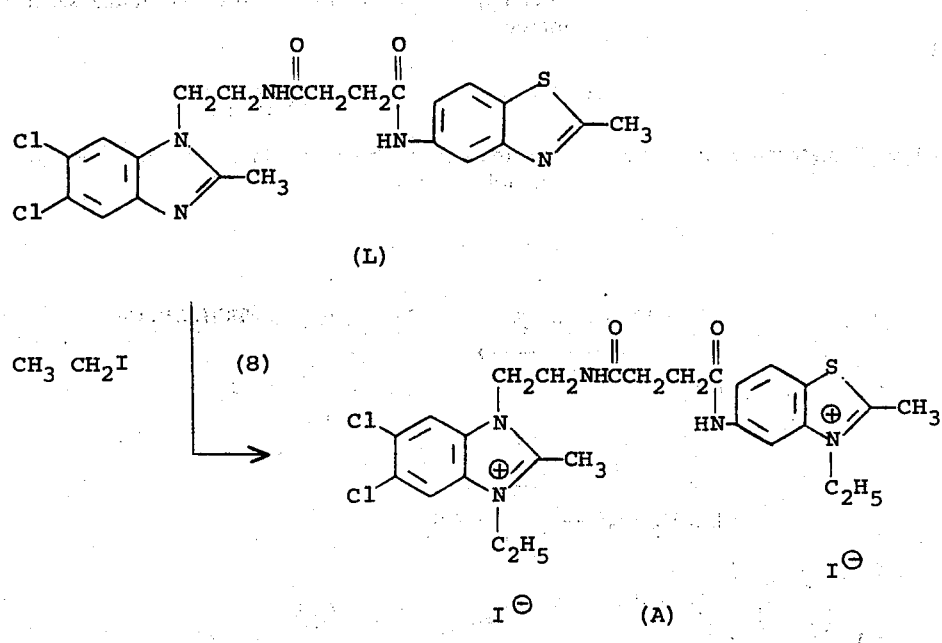

1. 226 g. of (D) was dissolved in 300 ml. of refluxing ethanol in a three-necked, 1000 ml. flask equipped with a mechanical stirrer. To this solution, 124 g. of 2-amino ethanol was added, at reflux, dropwise over a 30 minute period. The orange solution was refluxed for 16 hours, cooled and orange needles were collected and washed with ethanol and vacuum dried to yield 180 g. (72%) of E; m.p. 141°–145° C.

2. 124 g. of (E) was dissolved in 1000 ml. of hot 2-methoxy ethanol. To this was added 180 ml. of 12N HCl and 7 g. of a mixture of 10% Pd/90% C. This mixture was placed in a shaker and when hydrogen uptake ceased, it was removed. The bottle was removed from the shaker, heated on a steam bath until a clear solution formed and filtered. The filtrate was evaporated to dryness and crystals formed. 500 ml. of 5N HCl was added and 120 ml. of glacial acetic acid was added and refluxed for 7 hours. A brown solution resulted. On cooling tan crystals formed and were filtered off, washed with wateer, then dissolved in 700 ml. of hot methanol and NH₄OH was added until a pH of 9 was reached and then the solution was cooled. The white-tan crystals were filtered off, washed with water and vacuum dried to yield 83 g. (69%) of (F); m.p. 189°–192° C.

3. 18 g. of (F) was dissolved in 250 ml. of anhydrous pyridine. To this was added 18 g. of p-toluene sulfonyl chloride at room temperature. This solution was then stirred for 6 hours. During this time a white precipitate of pyridine. HCl precipitated. 20 ml. of $H_2O$ was added to hydrolyze any excess sulfonyl chloride. The solution was stirred for 15 minutes and then poured into 600 ml. of $H_2O$. A white solid crystallized out and was filtered off, washed well with water and vacuum dried to yield 26 g. (85%) of (G); m.p. 205°–210° C.

4. 16 g. of (G) was placed in 90 ml. of anhydrous DMF. To this mixture was added 8 g. of potassium phthalimide. This solution was stirred at room temperature for 1 hour under nitrogen, then heated to 75°–80° C. for 3 hours, cooled and was added to 600 ml. of $H_2O$. A white-tan solid precipitated which was filtered off, vacuum dried, then stirred in ether, filtered and vacuum dried to yield 150 g. (100%) of (H); m.p. 342°–343° C.

5. 28 g. of (H) were placed in 1700 ml. of ethanol and heated to reflux. To this mixture was added 8.2 g. of 64% hydrazine hydrate. This mixture was refluxed for 3 hours during which time solution resulted. The ethanol was removed under reduced pressure and 500 ml. of $CHCl_3$ was added. The resultant solid was removed (phthalhydrazide), the $CHCl_3$ was removed under reduced pressure, and 500 ml. of anhydrous acetone was added. The solid which didn't dissolve was removed (more phthalhydrazide). The acetone solution of (J) was brought to a volume of 700 ml.

6. 9 g. of succinic anhydride was added to the solution of (J) and the resultant solution was refluxed for 6 hours. During this time a white solid precipitated. This solid was filtered off and washed with acetone and vacuum dried to yield 22 g. (overall 92% yield) of (K); m.p. 213°–214° C.

7. 18 g. of (K) and 8.6 g. of 1-methyl-5-amino benzothiazole were dissolved in 750 ml. anhydrous ethanol under a nitrogen blanket at reflux. This was cooled to 40° and 12.6 g. of N-ethoxycarbonyl-2-ethoxycarbonyl-1,2-dihydroquinoline (EEDQ) was added. The solution was stirred at room temperature overnight during which a white solid precipitated. The solid was filtered off, stirred in acetone and vacuum dried to yield 17 g. of (L). The mother liquor was evaporated down, acetone was added and 3 g. more of (L) was collected (78% yield); m.p. 260°–263° C. When recrystallized from ethanol the m.p. was 268°–269° C.

8. 13 g. of (L) was placed in a 500 ml. "bomb" with 150 g. of ethyl iodide. This was sealed and heated to 130° for 72 hours. Ether was added to the cooled mixture and the solids ground up and filtered. This light yellow solid was washed well with ether and dried to yield 21 g. (100%) of (A) (m.p. 220°–221° C. after refluxing in isopropanol and vacuum drying). The product contained ½ mole water. An elemental analysis of (A) resulted in the following:

|  | C | H | % of Element O | N | Cl | S |
|---|---|---|---|---|---|---|
| Found | 38.91 | 3.87 | 4.12 | 8.60 | 8.72 | 3.90 |
| Calculated | 38.90 | 3.86 | 3.91 | 8.72 | 8.85 | 3.91 |

The bis-type quaternary salts of the invention may be employed as intermediates in the preparation of a large and diverse group of compounds, particularly the class comprising linked cyanine dyes and related compounds. It is contemplated that the invention in its broadest aspects is applicable to the various condensation reactions in which previously known bis-type quaternary salts have been employed, that is, those condensation reactions leading to bis, polymeric and pseudo-polymeric cyanine materials, for example, as disclosed in the previously cited patent literature. The various condensation reactings leading to cyanine dyes, e.g., 2,2′-cyanines; isocyanines; carbocyanines; dicarbocyanines; tri-carbocyanines; tri- and other polynuclear cyanines; etc.; and compounds related thereto, e.g., merocyanines, azocyanines, pseudocyanines, hemicyanines, apocyanines, styryl dyes, cinnamylidine derivatives, cyadiazines, cyazines, etc., are all well known to the art and need not be repeated in detail herein. For further synthetic information and details, reference is made to the technical literature, e.g., Hamer *Cyanine Dyes and Related Compounds*, Interscience Publishers, 1964, for general synthetic procedures and the patent literature, e.g., the aforementioned U.S. Pat. Nos. 2,425,722 and 3,622,317 for the various reactions of bis-type quaternary salts.

In general, the preparative procedures involve a condensation reaction in the presence of a basic condensing agent, between a bis-quaternary salt of the present invention having a pair of reactive methyl groups as indicated in the formulae above, and at least a second heterocyclic salt having a complementary reactive group which is capable of condensing with one or both of the aforementioned reactive methyl groups to form a cyanine dye or related compound. If double or bis compounds with only two cyanine segments are desired, the second heterocyclic salt may contain a single reactive group. The reaction in this case may be carried out by providing at least two mols of the second heterocyclic salt, one to condensate with each reactive methyl group of the bis-quaternary salt, therby completing each dye segment with the same heterocyclic ring system. Alternatively, one mol of the second heterocyclic salt may be condensed with one reactive methyl group of the double salt and one mol of a third and different heterocyclic salt may be condensed with the remaining reactive methyl group. "Polymeric" cyanine compounds, i.e., those having more than two repeating cyanine segments, on the other hand, may be prepared by using a second bis- or poly-quaternary salt, which may be the same as or different than the first. This reaction may be advantageously carried out by having the compounds in equimolar proportions.

The aformentioned basic condensing agent may comprise an organic amine, for example, tri-n-propylamine, tri-n-butylamine, triisoamylamine, triethylamine, trimethylamine, dimethylaniline, diethylaniline, pyridine, N-alkyl-piperidine, etc., and most preferably an organic tertiary amine having a dissociation constant greater than pyridine ($1 \times 10^{-5}$); an alkali metal carboxylate in a carboxylic anhydride, for example, sodium acetate in acetic anhydride; etc.; or an alkali metal hydroxide, for example, sodium hydroxide potassium hydroxide, etc. Preferably, the stated condensation reaction takes place in the presence of heat and in a substantially inert reaction medium such as lower molecular weight alcohol, for example, ethyl, n-propyl, isopropyl, n-butyl or isobutyl alcohol or methoxy ethanol; tricresylphosphate; or a phenol; or a reaction medium itself comprising the condensing agent such as pyridine.

In a preferred procedure, one mole of a bis-type quaternary salt of the invention may be condensed, in the presence of a basic condensing agent such as triethylamine, as previously described, with at least one mole of a heterocyclic compound of the formula:

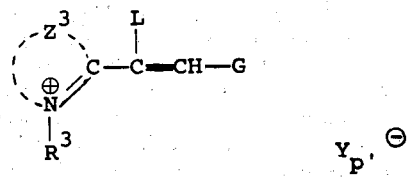

VI.

wherein $Z^3$ represents the atoms necessary to complete a heterocyclic ring system containing at least one 5- or 6-membered heterocyclic nucleus, preferably a ring system of the benzothiazole, benzimidazole, benzoxazole or benzoselenazole series; $R^3$ is a substituent such as the previously described lower alkyl, sulfoalkyl and carboxyalkyl substituents of Formulae I and II; G is a proton-seeking (negative) group adapted to condense with the active methyl group to form a tri-methine cyanine linkage such as for example, a β-anilino group, a β-alkyl mercapto group, a β-aryl mercapto group, a β-(p-tolusulfonanilido) group, etc.; L is a hydrogen atom or a lower alkyl group; Y is an acid anionic radical as previously defined; and $p'$ is 0 or 1. The product of the above reaction is what may be termed a "mono dye" in that a complete cyanine dye segment has been formed from one active methyl group and has linked thereto through the amide bridging group of the invention a quaternary salt segment having a reactive methyl group available for further dye condensation. Such mono dyes have been found to be effective spectral sensitizing dyes in their own right. Compound R of Example II hereinafter is representative of a "mono dye".

It should be understood that when reference herein, including the appended claims, is made to a ring system of a particular series, it is intended to include the named heterocyclic group and any of thee substituents or fused rings customarily present thereon in cyanine dyes and related compounds. As examples of such substituents known in the art, reference may be made of alkyl, e.g., 1 to 4 carbon alkyl; halogen, e.g., fluoro, bromo, chloro; alkoxy, e.g., methoxy, ethoxy, etc.; hydroxy; aralkyl, e.g., benzyl, phenethyl, etc.; aryl, e.g., phenyl; acyl, e..g., acetyl, propionyl, etc.; carboxyamido; cyano; carbamyl, sulfonamido; sulfamyl, thio, etc., as well as fused rings such as phenylene, pyridino, pyrimidino, etc.

As examples of dye intermediates within the scope of Formula VI, mention may be made of the following compounds.

M.

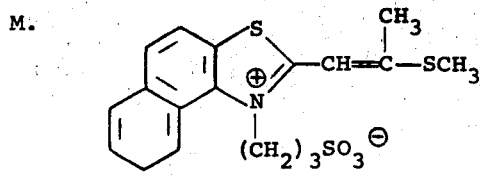

N.

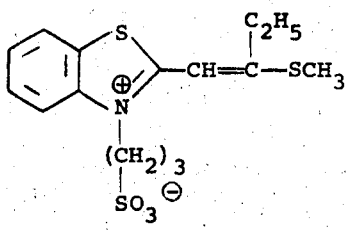

O.

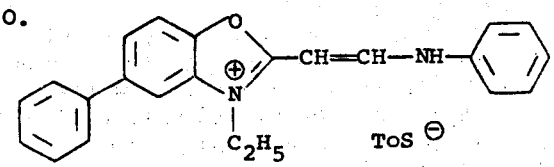

P.

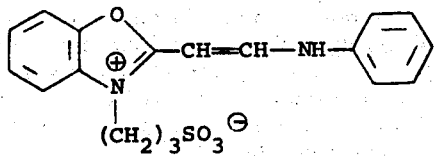

Q.

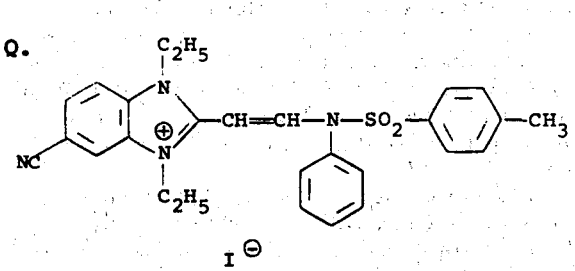

It has quite unexpectedly been discovered that the condensation reactions forming preferred linked double carbocyanine dyes from bis-type quaternary salts of the invention are apparently influenced by steric or other considerations since only a select few of the dye intermediates of Formula VI are suitable for condensation with both reactive methyl groups or with the remaining quaternary salt segment of the mono dye to form the corresponding double dyes. In other words, it has been found that many of the compounds of Formula VI which are suitable for condensation with the first reactive methyl group to form a mono dye either will not react with the remaining methyl group or attempted condensation results in the degradation of the mono dye.

One heterocyclic compound of Formula VI which has been found to be particularly suitable for condensation in the presence of a basic condensing agent with both reactive methyl groups on the bis-type quaternary salts of the invention and with the remaining methyl group of the mono dye to form double carbocyanine dyes may be represented by Formula VI when G is a β-anilino group and $Z^3$ is a ring system of the benzothiazole series, which includes those containing substituents on the benzothiazole nucleus, e.g., chloro, bromo, iodo, lower alkyl, carbalkoxy, acetanilide, etc.; and those containing a naphthathiazole nucleus. Compound S of Example II is a representative example of β-anilino vinyl benzothiazolium salts of this type.

The following examples will further illustrate the variety of ways in which the bis-type quaternary salts of the invention are useful in the synthesis of various cyanine dyes and related compounds, without intending to limit the invention in any way.

hours, filtered, refluxed in anhydrous ethanol for 3 hours, filtered and vacuum dried to yield 1.2 g. (95%). Results of an elemental analysis on the product are as follows:

|  | % of Element | | | | |
|---|---|---|---|---|---|
|  | C | H | %S | %Cl | %I |
| Found | 49.67 | 4.44 | 9.69 | 6.94 | 12.73 |
| Calculated | 50.05 | 4.41 | 9.42 | 6.95 | 12.50 |

EXAMPLE II

1. Preparation of a "mono dye" from a "double quat"

2. Preparation of a "double dye" from the "mono dye"

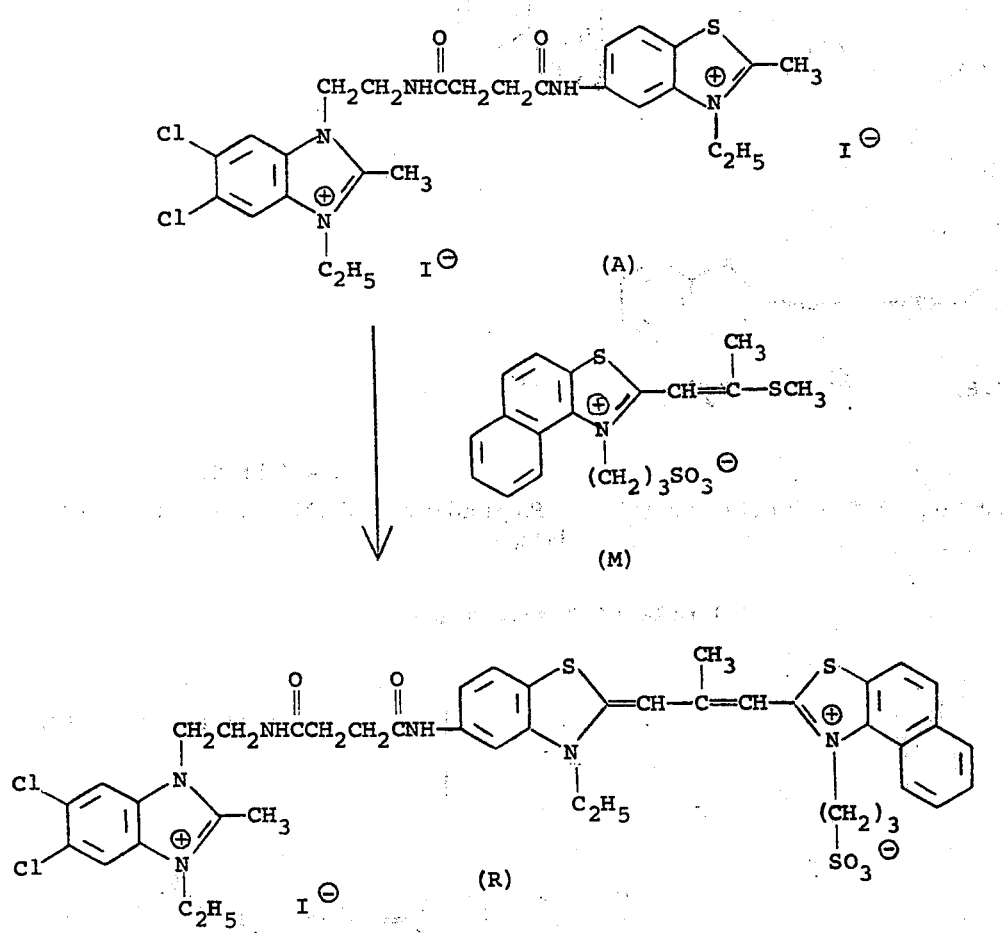

1 g. of (A) and 0.5 g. of (M) were heated to 80° C. in 20 ml. of DMSO. Triethylamine was added to this solution, resulting in an immediate color change to purple. The solution was heated to 85° C. for 12 minutes, then 50 ml. of isopropanol was added, the solution stirred for 5 minutes and then filtered. The resultant dye (R) was washed with isopropanol, then refluxed in isopropanol for 3 hours, filtered, refluxed in CHCl₃ for 16

1.0 g of (R) and 0.40 g. of (S) were dissolved in 20 ml. of sulfolane at 120° C. To this solution, 1 ml. of acetic anhydride and triethylamine was added and an immediate color change took place. The resultant mixture was heated 20 minutes and then 120 ml. of isopropanol was added. The resulting precipitate was filtered off, washed well with isopropanol and then refluxed in 100 ml. of isopropanol for 1 hour, filtered and vacuum Compound (R)
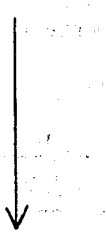 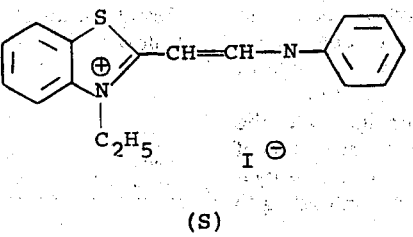
(S)
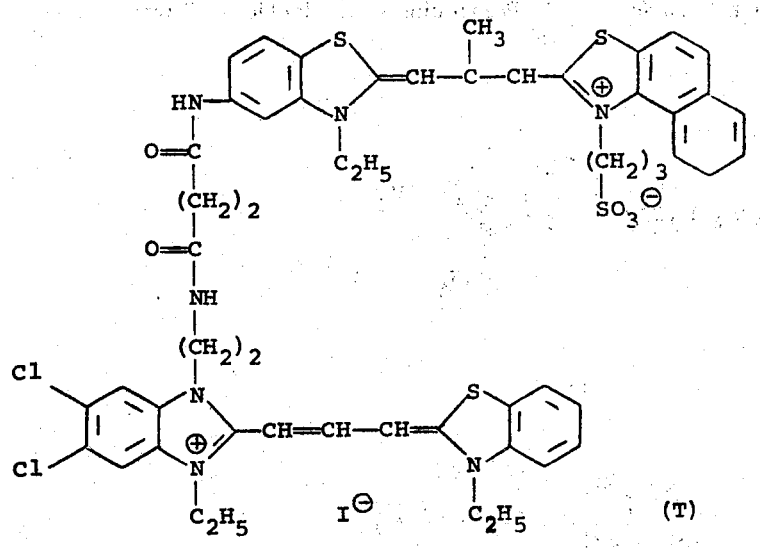
dried to yield about 1.0 g. (85% yield) of compound (T).
EXAMPLE III
Preparation of a "double dye" directly from a "double quat"
1 mole of Compound (A)
+ 2 moles of Compound (S)
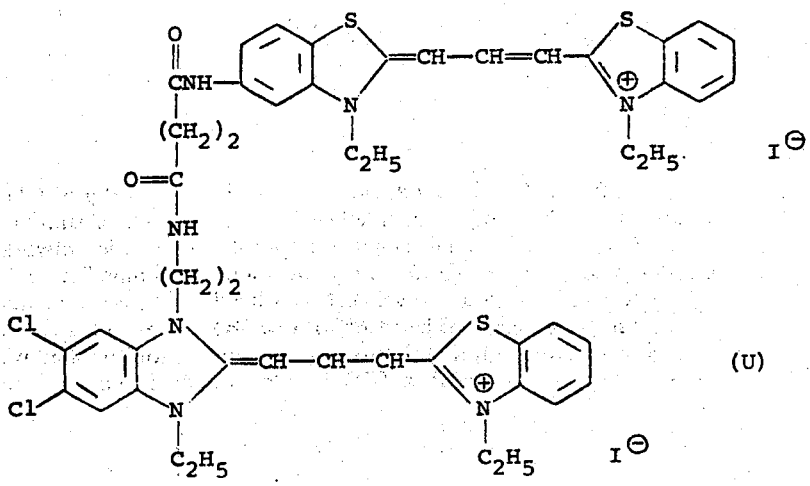

1 g. of (A) [see Example I] and 1.1 g. of (S) [see Example II] were dissolved in 25 ml. of sulfolane. To this solution, 2 ml. of acetic anhydride and triethylamine were added. An immediate color change to purple resulted, the solution was heated for 5 minutes at 115° C. and then 200 ml. of isopropanol was added. Whe cooled, a green solid (U) was filtered off, refluxed in isopropanol, filtered and vacuum dried.

It will be apparent to those skilled in the art from the above examples that the bis-type quaternary salts of the invention are quite versatile and that the above products and processes utilizing same may be varied without departing from the scope of the invention herein involved. Accordingly, it is intended that all matter contained in the above description and examples shall be interpreted as illustrative and not in a limiting sense.

What is claimed is:

1. A bis-type quaternary salt selected from the group consisting of compounds having the formulae:

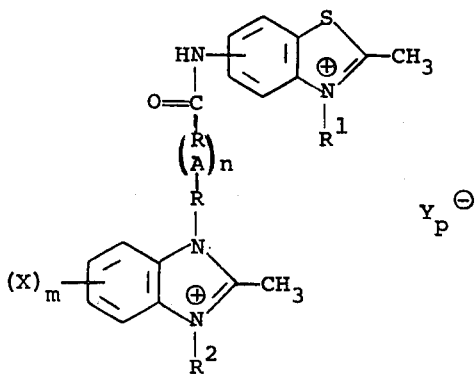

and

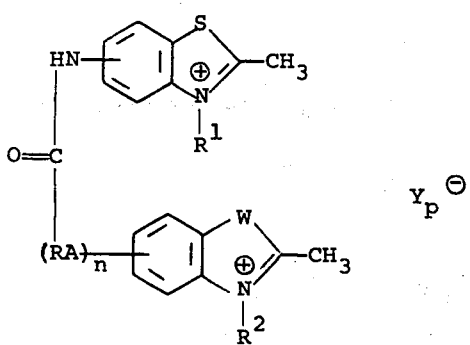

wherein R is an alkylene group having from 1 to 5 carbon atoms; A is a divalent amide group; $R^1$ and $R^2$ are each a lower alkyl group, a sulfoalkyl group or a carboxyalkyl group; W is S or N–T, wherein T is a lower alkyl group; X is a hydrogen atom, halogen atom, cyano group, or a carbalkoxy group; Y is an acid anionic radical; $n$ and $p$ are each 0, 1 or 2; and $m$ is 1 or 2.

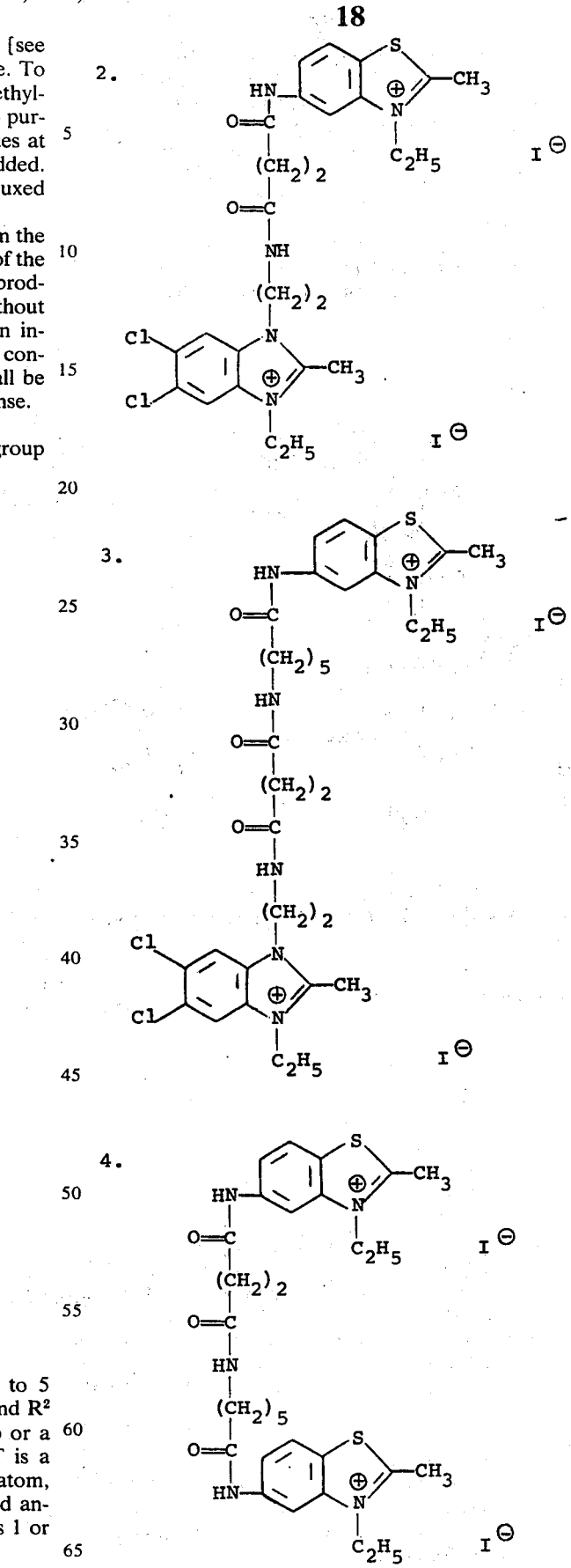

5. In a process for forming cyanine dyes and related compounds wherein a first heterocyclic quaternary salt intermediate having at least one reactive methyl group is condensed in the presence of a basic condensing agent with at least a second heterocyclic intermediate having a reactive group capable of dye condensation with said reactive methyl group, the improvement which comprises:

condensing said second heterocyclic intermediate with a bis-type quaternary salt selected from the group consisting of compounds having the formulae:

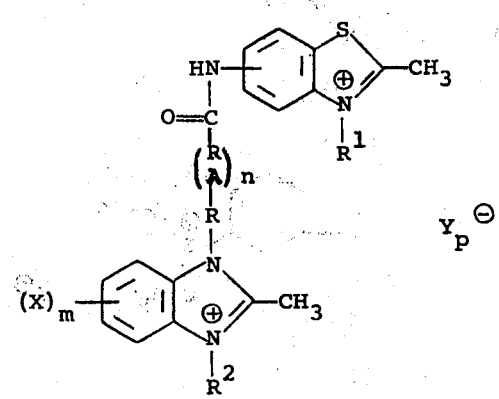

and

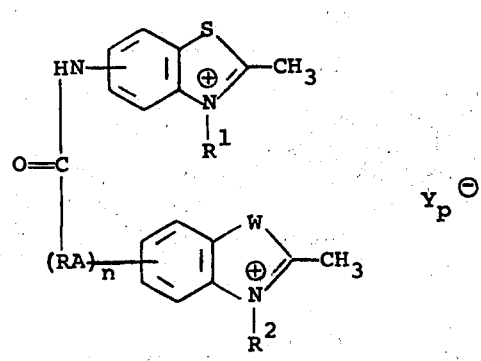

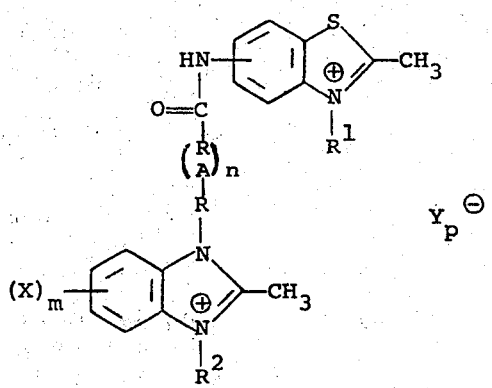

and

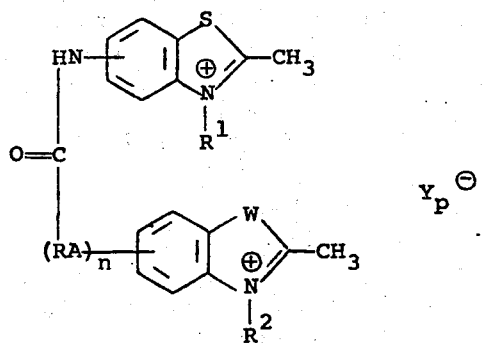

wherein R is an alkylene group having from 1 to 5 carbon atoms; A is a divalent amide group; $R^1$ and $R^2$ are each a lower alkyl group, a sulfoalkyl group or a carboxyalkyl group; W is S or N–T, wherein T is a lower alkyl group; X is a hydrogen atom, halogen atom, cyano group, or a carbalkoxy group; Y is an acid anionic radical; n and p are each 0, 1 or 2; and m is 1 or 2.

6. A process for the preparation of a cyanine or related dye which comprises:

condensing, in the presence of a basic condensing agent, one mole of a bis-type quaternary salt selected from the group consisting of compounds having the formulae:

wherein R is an alkylene group having from 1 to 5 carbon atoms; A is a divalent amide group; $R^1$ and $R^2$ are each a lower alkyl group, a sulfoalkyl group or a carboxyalkyl group; W is S or N–T, wherein T is a lower alkyl group; X is a hydrogen atom, halogen atom, cyano group, or a carbalkoxy group; Y is an acid anionic radical; n and p are each 0, 1 or 2; and m is 1 or 2; and at least one mole of a heterocyclic dye intermediate of the formula:

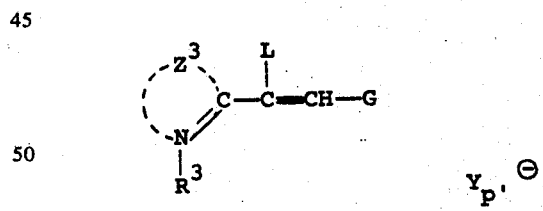

wherein $Z^3$ represents the atoms necessary to complete a heterocyclic ring system containing at least one 5- or 6-membered heterocyclic nucleus; $R^3$ is a lower alkyl group, a sulfoalkyl group or a carboxyalkyl group; G is a proton-seeking group adapted to condense with a reactive methyl group of said bis-type quaternary salt to form a trimethine cyanine linkage; L is a hydrogen atom or a lower alkyl group; Y is an acid anionic radical; and p' is 0 or 1.

7. A process as defined in claim 6 wherein G is a β-anilino group, as β-alkyl mercapto group, a β-aryl mercapto group or a β-(p-tolusulfonanilido) group.

8. A process as defined in claim 6 wherein $Z^3$ is a heterocyclic ring system of the benzothiazole, benzimidazole, benzoselenazole or benzoxazole series.

9. A process as defined in claim 6 wherein one mole of said dye intermediate is condensed with one mole of said bis-type quaternary salt to form a mono dye having one remaining reactive methyl group, which mono dye in turn is condensed in the presence of a basic condensing agent with one mole of said dye intermediate wherein $Z^3$ is a heterocyclic ring system of the benzothiazole series and G is a $\beta$-anilino group thereby to form a double carbocyanine dye.

10. A process as defined in claim 6 wherein two moles of said dye intermediate wherein $Z^3$ is a heterocyclic ring system of the benzothiazole series and G is a $\beta$-anilino group are condensed with one mole of said bis-type quaternary salt thereby to form a double carbocyanine dye.

* * * * *